United States Patent [19]

Takayanagi et al.

[11] Patent Number: 4,487,836

[45] Date of Patent: Dec. 11, 1984

[54] METHOD AND APPARATUS FOR DETECTING BOUNDARY SURFACE BETWEEN BLOOD PLASMA AND BLOOD CORPUSCLE SUSPENSION

[75] Inventors: Akitoshi Takayanagi, Kawasaki; Tokio Kano, Akishima, both of Japan

[73] Assignee: Olympus Optical Co. Ltd., Japan

[21] Appl. No.: 402,743

[22] Filed: Jul. 27, 1982

[30] Foreign Application Priority Data

Aug. 3, 1981 [JP] Japan .................. 56-121722

[51] Int. Cl.³ ............... G01N 27/02; G01N 33/48
[52] U.S. Cl. .................. 436/2; 73/863.01;
  73/863.21; 204/403; 324/65 R; 422/68;
  422/101; 436/63; 436/150; 436/177
[58] Field of Search ............ 324/65 R, 65 P;
  73/863.01, 863.21, 863.82; 436/63, 174, 150,
  177, 2; 422/101, 68; 204/403, 409

[56] References Cited

U.S. PATENT DOCUMENTS

| 3,635,094 | 1/1972 | Oberli . | |
| 4,055,799 | 10/1977 | Coster et al. | 204/403 X |
| 4,343,782 | 8/1983 | Shapiro | 436/63 |
| 4,368,423 | 1/1983 | Liburdy | 436/63 X |

FOREIGN PATENT DOCUMENTS 0039184 4/1978 Japan .................. 73/863.01

Primary Examiner—Arnold Turk
Attorney, Agent, or Firm—Parkhurst & Oliff

[57] ABSTRACT

A method and an apparatus for detecting a boundary surface between a blood plasma and a blood corpuscle suspension obtained after centrifuging are disclosed. An impedance across a pair of electrodes is measured by applying an A.C. voltage across the electrodes at such a frequency that impedances of the blood plasma and the blood corpuscle suspension are made greatly different from each other. When the impedance changes abruptly, it is determined that the electrodes have passed through the boundary surface.

15 Claims, 7 Drawing Figures

FIG.3
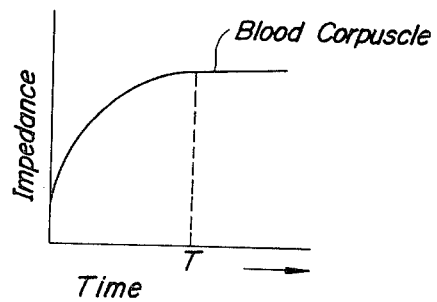
FIG.4A    FIG.4B
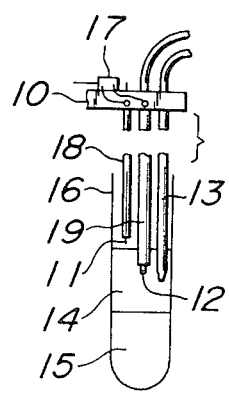 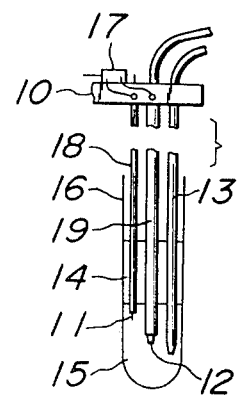

METHOD AND APPARATUS FOR DETECTING BOUNDARY SURFACE BETWEEN BLOOD PLASMA AND BLOOD CORPUSCLE SUSPENSION

BACKGROUND OF THE INVENTION

The present invention relates to a method and an apparatus for detecting a boundary surface between a blood plasma and a blood corpuscle suspension which have been separated by centrifuge. Such method and apparatus may be applied to an apparatus for delivering the plasma and corpuscle suspension separately.

In a conventional method, a difference of D.C. resistance between respective samples, for example, a serum and a clot was used to detect the boundary surface therebetween. FIG. 1 is a schematic view showing a known apparatus for detecting the boundary surface. As shown in FIG. 1, a sample contained in a test tube 1 includes a serum 2 and a clot 3 which are separated by centrifuge. In order to extract the serum 2, a pair of electrodes 4 provided in an electrically insulating tube 5 and a suction nozzle 6 are immersed into the sample. The tube 5 and nozzle 6 are secured to a holder 7 which moves up and down. While the electrodes 4 and the suction nozzle 6 are moved gradually downward, a resistance between electrodes 4 is measured in a continuous manner by applying a D.C. voltage across the electrodes 4. The boundary surface between the serum 2 and the clot 3 is detected when the resistance is changed abruptly. In this case, since the serum 2 is a liquid-like material having a low viscosity but the clot 3 is a gel-like material having a high viscosity, a resistance ratio of the serum 2 to the clot 3 becomes large about one to several tens, so that the boundary surface can be easily and precisely detected. However, if an anticoagulant is added to the blood sample, the resistance of a blood corpuscle suspension is low and thus, the resistance ratio of a blood plasma to a blood corpuscle suspension is about 1 to 1.1; therefore it is not possible to detect the boundary surface between the blood plasma and blood corpuscle suspension easily and correctly by the known method.

SUMMARY OF THE INVENTION

The present invention has for its object the obviation of the drawbacks mentioned above and the provision of a novel and useful method for detecting accurately and stably a boundary surface between a blood plasma and a blood corpuscle suspension.

According to the invention, a method for detecting a boundary surface between a blood plasma and a blood corpuscle suspension of a sample contained in a vessel comprises, a step of immersing a pair of electrodes into the sample;
a step of applying across the electrodes an A.C. voltage having such a frequency that an impedance of the blood plasma is greatly different from that of the blood corpuscle suspension; and
a step of detecting an impedance across said electrodes, whereby the boundary surface between the blood plasma and blood corpuscle suspension is detected when the impedance changes abruptly.

Another object of the invention is to provide an apparatus for detecting a boundary surface which can perform the method mentioned above with a simple construction.

According to the invention, an apparatus for detecting a boundary surface between a blood plasma and a blood corpuscle suspension of a sample contained in a vessel comprises, first and second electrodes;
means for immersing said first and second electrodes into the sample;
means for applying across said first and second electrodes an A.C. voltage having a frequency at which an impedance of the blood plasma is greatly different from that of the blood corpuscle suspension; and
means for detecting an abrupt change of an impedance across the electrodes to detect the boundary surface between the blood plasma and the blood corpuscle suspension.

BRIEF DESCRIPTION OF THE DRAWINGS

FIG. 3 is a graph depicting a response characteristic of a corpuscle suspension impedance measurement;

FIGS. 4A and 4B are schematic views showing one embodiment of the apparatus according to the invention.

DESCRIPTION OF THE PREFERRED EMBODIMENTS

Figure 1:
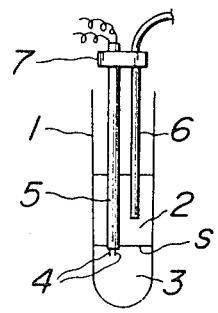
FIG. 1 is a schematic view showing one embodiment of a conventional apparatus for detecting a boundary surface.
Figure 2:
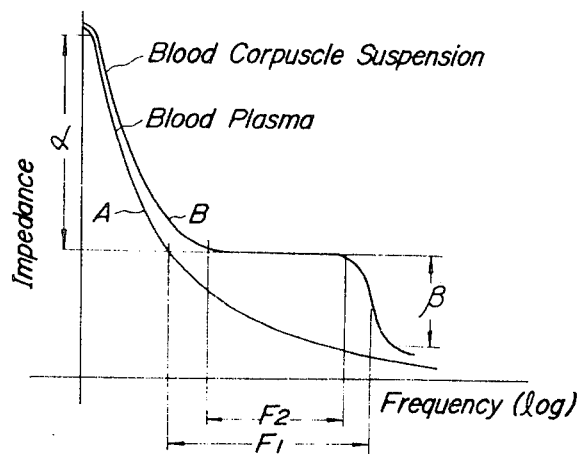
FIG. 2 is a graph illustrating frequency characteristic curves of impedance of a blood plasma and a blood corpuscle suspension.

FIG. 2 is a graph showing frequency characteristic curves of impedance of a blood plasma and a blood corpuscle suspension. Both the blood plasma and corpuscle suspension are liquids each including organic substances. Generally, a liquid including organic substances such as blood cells and proteins has a high dielectric loss tangent (tan $\delta$) characteristic as compared with pure water, and a capacitance thereof per unit area becomes large accordingly. The impedance of material having a capacitance is decreased corresponding with an increase of frequency, and thus the impedance of each of the blood plasma and corpuscle suspension is decreased corresponding to the frequency as shown in FIG. 2. As shown by a curve A, the impedance of blood plasma is decreased smoothly, but the impedance of the corpuscle suspension has a flat region as shown by a curve B. Such a characteristic is called dispersion, and electrical characteristics such as frequency vs. impedance are varied abruptly. In biochemistry, $\alpha$ and $\beta$ regions shown in FIG. 2 are called $\alpha$-dispersion and $\beta$-dispersion regions, respectively. In the preferred embodiment according to the invention, the flat portion in the $\beta$-dispersion region $\beta$ is utilized for detecting the boundary surface between the blood plasma and the corpuscle suspension. That is to say, an impedance of the blood plasma and corpuscle suspension is measured by applying across electrodes an A.C. voltage having a frequency in a frequency range $F_1$, particularly in a frequency range $F_2$, as shown in FIG. 2. In order to detect the boundary surface stably and easily, it is sufficient that the impedance ratio of blood plasma to corpuscle suspension is greater than 1 to 2. Then, the frequency range $F_1$ may be set to about 30 Hz to 400 KHz. Moreover, in the frequency range $F_2$ of about 10 KHz to 50 KHz, the maximum value of the impedance ratio of about 1:7 may be obtained. Strictly speaking, the impedance ratio is varied slightly corresponding to difference in amounts of respective samples, but such difference is negligible as far as a biochemical analysis is concerned.

FIG. 3 is a graph showing a response characteristic of the impedance of a blood corpuscle suspension. As shown in FIG. 3, it takes a relatively long time T until the measured impedance of a corpuscle suspension reaches a constant value after the electrodes are immersed into the corpuscle suspension. Contrary to this, a time constant in the blood plasma measurement is extremely small as compared with that of corpuscle measurement and thus negligible. However, the lag time T in the impedance measurement for the corpuscle suspension is long enough to influence the detection of the boundary surface. Therefore, in case of sucking the blood corpuscle suspension by moving the suction nozzle downward and dipping a tip portion thereof into the corpuscle suspension, it is necessary to determine a descending speed and a stop timing of the suction nozzle taking into account a moving distance corresponding to the time constant T.

FIGS. 4A and 4B are schematic views showing one embodiment of the apparatus according to the invention. In this embodiment, an electrode 11 covered with an electrically insulating coating 18 except for a tip end of the electrode, a blood corpuscle suction nozzle 12 made of metal and also covered with an insulating coating 19 except for a top end of the nozzle, and a blood plasma suction nozzle 13 are secured to a holder 10. In this case, the tip end of the nozzle 13 is slightly lower than the tip end of the nozzle 12 and the exposed electrode 11 is substantially higher than the nozzle 12. In a test tube there are contained a blood plasma 14 and a blood corpuscle suspension 15 which have been separated by a centrifuge. The holder 10 is first moved downward, the nozzles 13 and 12 are successively dipped into the blood plasma 14. In a course of this downward movement, the holder 10 is stopped when it is detected that the electrode 11 reaches the blood plasma 14 by detecting an impedance change between the electrode 11 and the nozzle 12 by means of an detector 17, while an A.C. voltage having a frequency in the range $F_2$ in FIG. 2 is applied across the electrode 11 and nozzle 12. At this time, the nozzle 13 is immersed into the blood plasma 14 by a given length and a given amount of the blood plasma is sucked by the suction nozzle 13. After sucking the given amount of the blood plasma 14, the holder 10 is further moved downward and is stopped again when the electrode 11 is immersed into the blood corpuscle suspension 15. That is to say, the impedance between the electrode 11 and the nozzle 12 is changed clearly when the electrode 11 has passed through the boundary between the blood plasma 14 and the corpuscle suspension 15, and after this change is detected by the detector 17, the downward movement is stopped. At this position, a given amount of the blood corpuscle suspension 15 is sucked by means of the nozzle 12.

As explained above, the nozzle 12 is extended downward with respect to the electrode 11 by a certain distance and this distance must be suitably determined while taking into account the time constant T and a nozzle descending speed. That is to say, after the nozzle 12 has passed through the boundary between the plasma 14 and the corpuscle suspension 15, the nozzle 12 must be stopped at such a position that the given amount of the corpuscle suspension 15 can be sucked correctly as illustrated in FIG. 4B.

Figure 5:
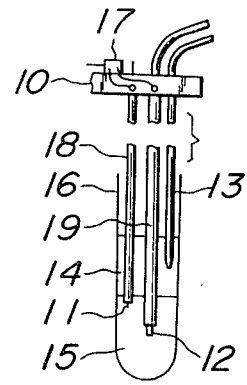
FIGS. 5 and 6 are schematic views illustrating other embodiments of the apparatus according to the invention.

FIG. 5 is a schematic view showing another embodiment of the apparatus according to the invention. In this embodiment, the electrode 11 and nozzles 12 and 13 are arranged so as to suck simultaneously the blood plasma 14 and the blood corpuscle suspension 15. For this purpose, the tip portion of nozzle 13 is set upward by a given distance with respect to the tip of nozzle 12. In this embodiment, when an abrupt change of the impedance due to the immersion of the electrode 11 into the corpuscle suspension 15 is detected by the detector 17, the holder 10 is stopped to move downward. At this position, the blood corpuscle suspension 15 is sucked by the nozzle 12 and, at the same time, the blood plasma 14 is sucked by the nozzle 13. Also in this embodiment, the top position of the holder 10 must be determined while taking into account the time constant T and the level difference between the electrode 11 and nozzle 12.

Figure 6:
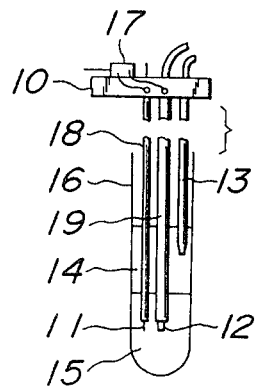

FIG. 6 is a schematic view showing still another embodiment of the apparatus according to the invention. In this embodiment, the time constant T is positively utilized to stop the holder 10 at the position most suitable for sucking the blood corpuscle suspension 15. Also in this embodiment the blood plasma 14 and the blood corpuscle suspension 15 are sucked at the same time. That is to say, the electrode 11 and the nozzle 12 are arranged at the same level and the holder 10 is stopped when the abrupt impedance change is detected by the detector 17 after the time T from a time instant when the electrode 11 has passed through the boundary surface. During this time period T, the holder 10, and thus the nozzle 12 are moved downward by a distance $V \times T$, whereas V is the descending velocity. Then, by suitably selecting the descending velocity V, it is possible to stop the nozzle 12 at the position most suitable for sucking the blood corpuscle 15. It should be noted that a distance between the nozzles 12 and 13 is so determined that at the stop position the nozzle 13 is situated at the most suitable position for sucking the blood plasma 14.

As explained above in detail, according to the invention, since the impedance measurement is effected with the A.C. voltage having such a frequency that the impedance of the blood corpuscle suspension is greatly different from that of the blood plasma, the boundary surface between the blood plasma and the blood corpuscle suspension can be detected stably and precisely.

What is claimed is:

1. A method for detecting a boundary surface between a blood plasma and a blood corpuscle suspension of a sample contained in a vessel comprising:
   immersing a pair of electrodes into the sample;
   applying an AC voltage across said electrodes having a frequency such that the impedance between the electrodes is in a $\beta$-dispersion region where the impedance of the blood plasma is substantially different from that of the blood corpuscle suspension;
   moving the electrodes relative to the samiple while the electrodes are immersed in the sample; and
   detecting an abrupt change in the impedance across said electrodes in order to detect the boundary surface between the blood plasma and blood corpuscle suspension in said sample.

2. A method according to claim 1, wherein said electrodes are immersed into the sample at a speed which is determined with respect to a time constant T during which the measured impedance of the blood corpuscle suspension reaches a constant value.

3. A method according to claim 1, wherein a liquid level of the blood plasma is also detected by detecting an abrupt change of the impedance across said electrodes.

4. A method according to claim 1 wherein said frequency is set at a frequency range from about 30 Hz to 400 KHz.

5. A method according to claim 1 wherein said frequency is set at a frequency range from about 10 KHz to 50 KHz.

6. An apparatus for detecting a boundary surface between a blood plasma and a blood corpuscle suspension in a sample contained in a vessel comprising:
   first and second electrodes;
   means for immersing said first and second electrodes into a sample;
   means for applying across said first and second electrodes an AC voltage having a frequency such that the impedance between the electrodes is in the $\beta$-dispersion region where the impedance of the blood plasma is substantially different from the impedance of the blood corpuscle suspension;
   means for moving the electrodes relative to the sample while the electrodes are immersed in the sample, and
   means for detecting an abrupt change of impedance across the electrodes in order to detect the boundary surface between the blood plasma and the blood corpuscle suspension in a sample.

7. An apparatus according to claim 6, wherein said first electrode comprises an electrically conductive wire and an electrically insulating coating applied on an outer surface of the conductive wire except for its tip portion.

8. An apparatus according to claim 7, wherein said second electrode comprises a blood corpuscle suspension suction nozzle made of metal and an electrically insulating coating applied on an outer surface of the nozzle except for a tip portion thereof.

9. An apparatus according to claim 8, further comprising a suction nozzle for sucking said blood plasma.

10. An apparatus according to claim 9, wherein said means for immersing comprises a holder and wherein said first and second electrodes and blood plasma suction nozzle are secured to said holder which is moved up and down.

11. An apparatus according to claim 10, wherein a tip portion of the second electrode is made lower than a tip portion of the first electrode, and a tip portion of the blood plasma sucking nozzle is made lower than the tip portion of the second electrode.

12. An apparatus according to claim 10, wherein a tip portion of the second electrode is made lower than a tip portion of the first electrode, and a tip portion of the blood plasma sucking nozzle is made higher than the tip portion of the first electrode.

13. An apparatus according to claim 10, wherein tip portions of said first and second electrodes are fixed at the same level, and a tip portion of the blood plasma sucking nozzle is made higher than the tip portions of the electrodes.

14. A method for detecting a boundary surface between a blood plasma and a blood corpuscle suspension of a sample contained in a vessel comprising:
   immersing a pair of electrodes in a sample including a blood plasma and a blood corpuscle suspension separated by a boundary surface;
   applying an AC voltage across said electrodes at a frequency such that the impedance presented between the electrodes by the blood plasma at said frequency is substantially different from the impedance presented between the electrodes by the blood corpuscle suspension at said frequency;
   moving said pair of electrodes within said sample; and
   detecting the impedance across said electrodes to sense an abrupt change in said impedance in order to detect the boundary surface between the blood plasma and blood corpuscle suspension in said sample.

15. An apparatus for detecting a boundary surface between a blood plasma and a blood corpuscle suspension in a sample contained in a vessel comprising:
   first and second electrodes;
   means for immersing said first and second electrodes into a sample;
   means for applying an AC voltage across said first and second electrodes at a frequency such that the impedance presented by a blood plasma between said electrodes is substantially different from the impedance presented by a blood corpuscle suspension between said electrodes;
   means for moving the electrodes relative to the sample while the electrodes are immersed in the sample; and
   means for detecting impedance across said first and second electrodes to sense an abrupt change in impedance in order to detect a boundary surface between a blood plasma and a blood corpuscle suspension in a sample.

* * * * *